(12) United States Patent  
Ashibe

(10) Patent No.: US 6,381,489 B1  
(45) Date of Patent: *Apr. 30, 2002

(54) MEASURING CONDITION SETTING JIG, MEASURING CONDITION SETTING METHOD AND BIOLOGICAL INFORMATION MEASURING INSTRUMENT

(75) Inventor: Emi Ashibe, Kyoto (JP)

(73) Assignee: Kyoto Daiichi Kagaku Co., Ltd., Kyoto (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/068,033

(22) PCT Filed: Oct. 30, 1996

(86) PCT No.: PCT/JP96/03181

§ 371 Date: Jul. 7, 1998

§ 102(e) Date: Jul. 7, 1998

(87) PCT Pub. No.: WO97/16117

PCT Pub. Date: May 9, 1997

(30) Foreign Application Priority Data

Oct. 31, 1995 (JP) .............................................. 7-319441

(51) Int. Cl.⁷ ................................................. A61B 5/00
(52) U.S. Cl. ......................... 600/476; 600/473; 600/344
(58) Field of Search ................................. 600/310, 473, 600/476, 344; 356/432

(56) References Cited

U.S. PATENT DOCUMENTS 4,515,165 A * 5/1985 Carroll ....................... 128/664

(List continued on next page.)

FOREIGN PATENT DOCUMENTS

EP          0 374 190 B1      6/1990    ............. A61B/5/00

(List continued on next page.)

OTHER PUBLICATIONS

Dialog File 347 (JAPIO) English Language Patent Abstract for JP 5–317295 A, published Dec. 3, 1993, p. 1.
Dialog File 347 (JAPIIO) English Language Patent Abstract for JP 7–329971 A, published Dec. 19, 1995, p. 1.
Japanese Patent Office, "Patent Abstracts of Japan", Abstract for JP Patent Publication No. 62185126 A, published Aug. 13, 1987, p. 1.

(List continued on next page.)

*Primary Examiner*—Marvin M. Lateef
*Assistant Examiner*—Eleni Mantismercader
(74) *Attorney, Agent, or Firm*—Sterne, Kessler, Goldstein & Fox PLLC

(57) ABSTRACT

A measurement condition setting fixture 2 is secured to a measurement site 1 of a living body prior to the measurement. At the time of measurement, a light irradiation section 3 and a light receiving section 5 of a measuring optical system are respectively attached and secured to a light irradiation section securing section 10 and a light receiving section securing section 11 of the measurement condition setting fixture 2. Thus, the measurement site 1 and the measuring optical system are secured to each other, and desirable measurement conditions can be realized. Moreover, the measurement conditions can be maintained throughout the measurement. After the measurement is completed, the measurement site 1 can be removed from the measuring optical system by detaching the light irradiation section 3 and the light receiving section 5 from the light irradiation section securing section 10 and the light receiving section securing section 11. When the measurement is performed again, the desirable measurement conditions can be reproduced merely by attaching the light irradiation section 3 and the light receiving section 5 to the light irradiation section securing section 10 and the light receiving section securing section 11.

32 Claims, 8 Drawing Sheets

U.S. PATENT DOCUMENTS

| | | | |
|---|---|---|---|
| 4,559,557 A | 12/1985 | Keyes et al. | 358/111 |
| 4,805,623 A | 2/1989 | Jöbsis | 600/328 |
| 4,830,014 A * | 5/1989 | Goodman et al. | 128/665 |
| 4,883,963 A | 11/1989 | Kemeny et al. | 250/339 |
| 5,039,855 A | 8/1991 | Kemeny et al. | 250/339 |
| 5,224,478 A * | 7/1993 | Sakai et al. | 128/633 |
| 5,226,417 A | 7/1993 | Swedlow et al. | 128/633 |
| 5,435,309 A | 7/1995 | Thomas et al. | 128/633 |
| 5,444,528 A | 8/1995 | Puschell | 356/73 |
| 5,475,221 A | 12/1995 | Wang | 250/339.07 |
| 5,477,321 A | 12/1995 | Johnson | 356/319 |
| 5,598,842 A | 2/1997 | Ishihara et al. | 128/637 |
| 5,879,373 A * | 3/1999 | Roper et al. | 606/344 |
| 5,949,540 A | 9/1999 | Matsuoka et al. | 356/326 |

FOREIGN PATENT DOCUMENTS

| | | | |
|---|---|---|---|
| EP | 0 641 542 A2 | 3/1995 | A61B/5/00 |
| EP | 0 722 691 A1 | 7/1996 | A61B/5/00 |
| JP | 54-77491 | 6/1979 | A61B/10/00 |
| JP | 60-207020 | 10/1985 | G01J/3/42 |
| JP | 61-163602 | 7/1986 | H01C/17/28 |
| JP | 61-165519 | 10/1986 | G02B/27/00 |
| JP | 62-123526 | 8/1987 | G01J/3/10 |
| JP | 62-185126 | 8/1987 | G01J/3/02 |
| JP | 63-171329 | 7/1988 | G01J/3/18 |
| JP | 1-316724 | 12/1989 | G02F/1/33 |
| JP | 2-24102 | 7/1990 | G02F/1/11 |
| JP | 3-500207 | 1/1991 | G01N/21/27 |
| JP | 3-138537 | 6/1991 | G01J/3/02 |
| JP | 4-76517 | 12/1992 | H01S/3/10 |
| JP | 6-201468 | 7/1994 | G01J/3/12 |
| JP | 7-55565 | 3/1995 | G01J/3/42 |
| JP | 5-317295 | 12/1995 | A61B/5/14 |
| JP | 7-329971 | 12/1995 | B65D/19/26 |
| JP | 8-178751 | 7/1996 | G01J/3/44 |
| JP | 8-215180 | 8/1996 | A61B/5/14 |
| WO | WO 89/01758 | 3/1989 | A61B/5/00 |

OTHER PUBLICATIONS

Dialog File 348 (EPO) English Language Patent Abstract for EP 722691 A1, published Jul. 24, 1996, p. 1.

Japanese Patent Office, "Patent Abstracts of Japan", Abstract for JP Patent Publication No. 63171329 A, published Jul. 15, 1988, p. 1.

Japanese Patent Office, "Patent Abstract of Japan", Abstracts for JP Patent Publication No. 62172777 A, published Jul. 29, 1987, p. 1.

Japanese Patent Office, "Patent Abstract of Japan", Abstracts for JP Patent Publication No. 01316724 A, published Dec. 21, 1989, p. 1.

Japanese Patent Office, "Patent Abstracts of Japan", Abstract for JP Patent Publication No. 06201468 A, published Jul. 19, 1994, p. 1.

Japanese Patent Office, "Patent Abstracts of Japan", Abstract for JP Patent Publication No. 03138537 A, published Jun. 12, 1991, p. 1.

Dialog File 348 (EPO) English Language Patent Abstract for EP 722691 A1, published Jul. 24, 1996, p. 1.

Japanese Patent Office, "Patent Abstracts of Japan", Abstract of JP Patent Publication No. 60207020 A, published Oct. 18, 1985, p. 1.

Japanese Patent Office, "Patent Abstracts of Japan", Abstract for JP Patent Publication No. 07055565 A, published Mar. 3, 1995, p. 1.

* cited by examiner

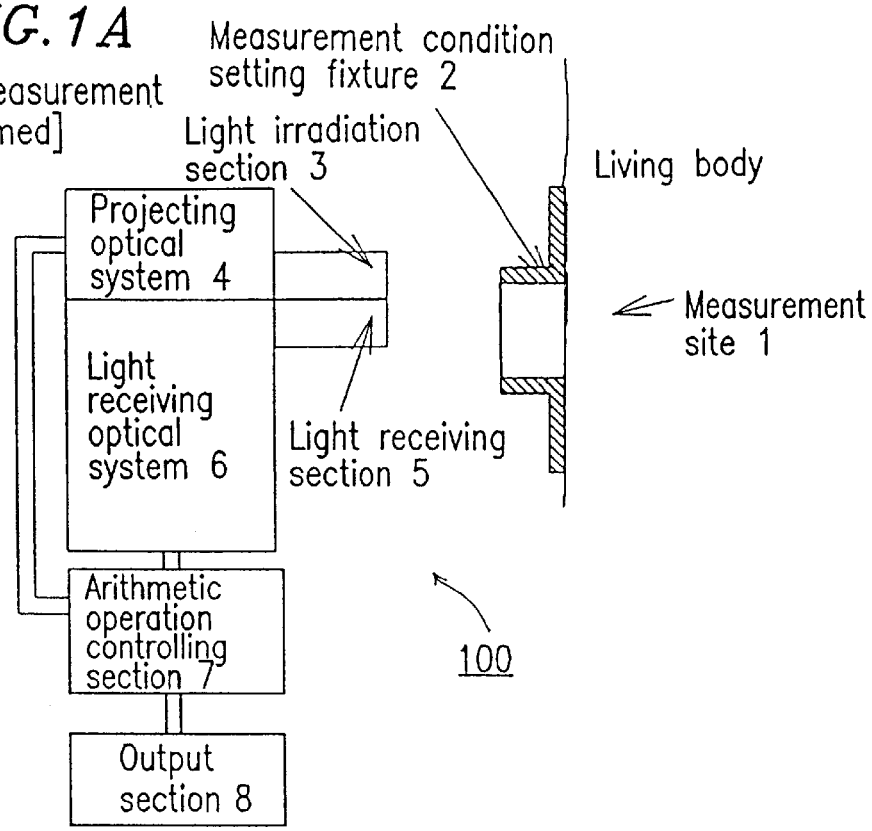
FIG. 1A [When no measurement is performed]
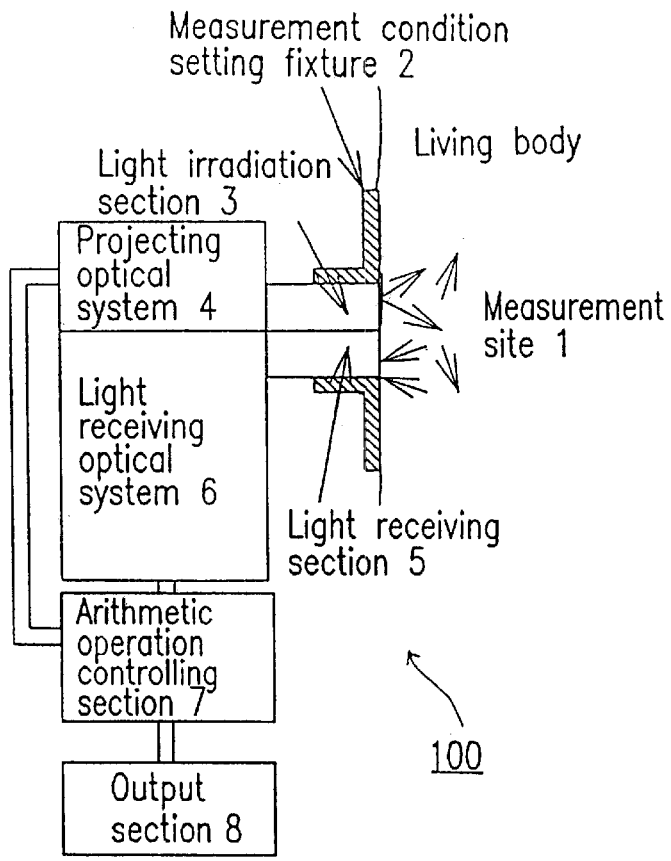
FIG. 1B [At the time of measurement]

FIG.4A [When no measurement is performed]
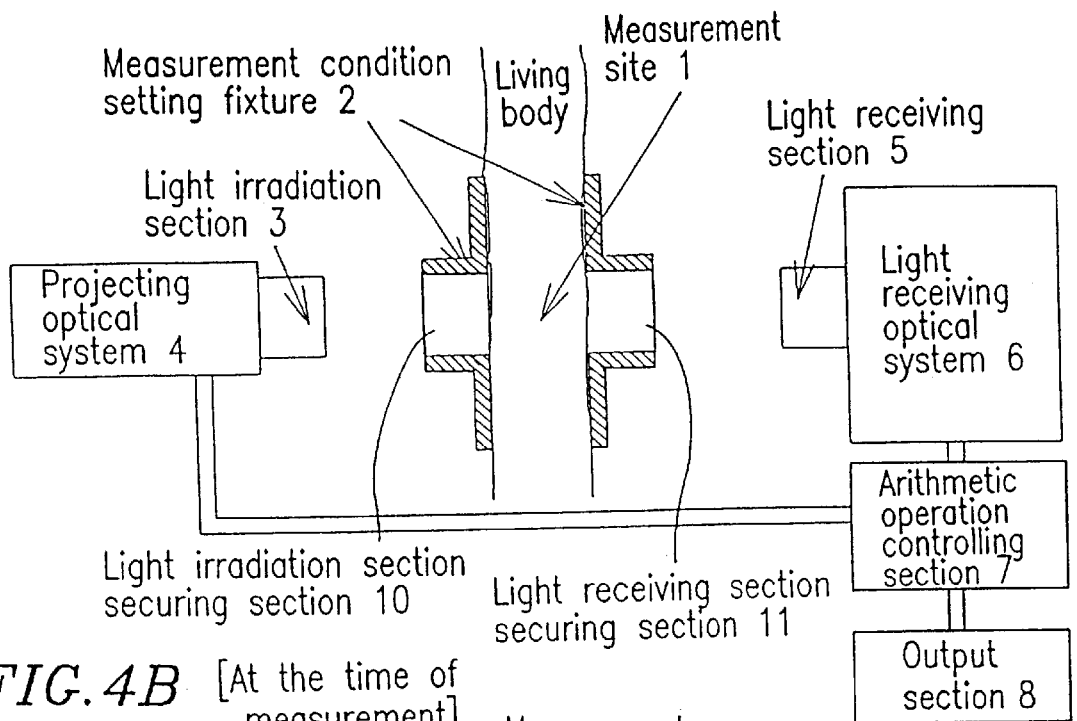
FIG.4B [At the time of measurement]
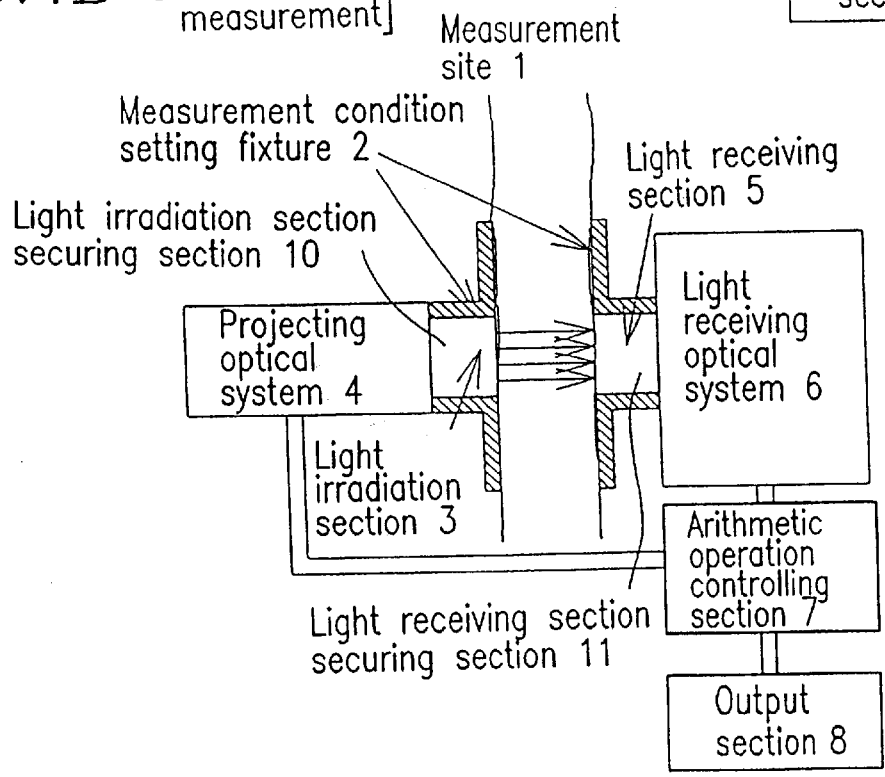

301 —■— Measured without securing the measurement site to the measuring optical system.
302 —♦— Measured with the measurement site being secured to the measuring optical system.
303 —□— Measured using the measurement condition setting fixture.

401 — Measured without securing the measurement site to the measuring optical system.
402 — Measured with the measurement site being secured to the measuring optical system.
403 — Measured using the measurement condition setting fixture.

Measurement site 1

Measurement site 1

MEASURING CONDITION SETTING JIG, MEASURING CONDITION SETTING METHOD AND BIOLOGICAL INFORMATION MEASURING INSTRUMENT

TECHNICAL FIELD

The present invention relates to a measurement condition setting fixture used in measurement of living body information for measuring living body information in a non-invasive manner, using transmitted light or reflected light obtained by irradiating a living body with light. In particular, the present invention relates to a measurement condition setting fixture, a measurement condition setting method, and a living body information measuring apparatus for setting measurement conditions, which include a site at which a measurement is to be taken and a relative position of the site at which a measurement is to be taken with respect to a measuring optical system, at desirable conditions at the time of measurement and for detaching the site at which a measurement is to be taken from the measuring optical system when no measurement is performed.

BACKGROUND ART

In general, in optical measurement for irradiating a living body with light and obtaining living body information based on transmitted or reflected light, even a slight change in the site irradiated by light at which a measurement is to be taken (hereinafter, referred to simply as a "measurement site") is a significant cause of error. Accordingly, in order to perform precise measurement, it is required to maintain measurement conditions such as the measurement site, the incident position and angle of light with respect to the measurement site, the position and angle at which the transmitted or reflected light from the measurement site is received, and the like.

In order to maintain the measurement conditions, it is ideal to keep the living body secured to the measuring apparatus throughout the measurement.

However, in the case where the living body is secured to the measuring apparatus, many inconveniences occur when the measurement takes a long time or a routine measurement is performed, such that the person undergoing the measurement cannot be away from the measuring apparatus or only one person can undergo the measurement by one measuring apparatus.

Moreover, since the surface of the living body is generally soft, repetition of attachment and detachment of the measuring apparatus with respect to the living body causes an error in the measurement conditions. For example, in the case where a method of using a clip-type measuring probe or a method of securing the measuring probe to the measurement site with a two-sided adhesive tape is used, the measurement site of the living body can be detached from the optical system of the measuring apparatus except when the measurement is performed. However, it is very difficult to accurately return to the previous location of the measurement site, i.e., to accurately attach the probe to the previous measurement site, in order to perform the measurement again.

As methods for accurately returning to the location of the measurement site, a method of marking the measurement site of the living body and visually determining the measurement site based on the marking, and a method of taking a pattern of the measurement site in advance and determining the measurement site using the pattern have been proposed. By either method, however, it is difficult to return to the location of the measurement site due to the softness of the living body. By the latter method, the same number of patterns as that of the measurement sites are required. In the case where the measurement site is deformed, the pattern cannot be used.

The present invention, which has been made under these circumstances, has the objectives of (1) providing a simple measurement condition setting fixture for easily and accurately setting measurement conditions, which include a measurement site and a relative position of the measurement site with respect to the measuring optical system, at desirable conditions at the time of measurement and for detaching the measurement site from the measuring optical system when no measurement is performed, and a measurement condition setting method utilizing the same, and (2) providing a living body information measuring apparatus for providing highly precise measurement values with little deviation.

DISCLOSURE OF INVENTION

A measurement condition setting fixture according to the present invention for setting measurement conditions including a positional relationship between a prescribed site of a living body and a measuring optical system at desirable conditions, in measurement of living body information including irradiating the prescribed site with light from the measuring optical system and obtaining living body information based on the light obtained from the prescribed site, the measurement condition setting fixture comprising a measurement site securing section attached to the prescribed site; and a measuring optical system securing section, to which a part of the measuring optical system is detachably attachable, for securing the part of the measuring optical system and the prescribed site in a prescribed positional relationship when the part of the measuring optical system is coupled to the measuring optical system, wherein the part of the measuring optical system is coupled to the measuring optical system securing section at the time of measurement, thereby realizing the desirable measurement conditions, and the part of the measuring optical system is detached from the measuring optical system securing section when no measurement is performed. Thus, the above-described objectives are achieved.

The part of the measuring optical system may include a light irradiation section for irradiating the prescribed site of the living body with light to be directed thereto, and the light irradiation section may be coupled to the measuring optical system securing section at the time of measurement, thereby securing the light irradiation section and the prescribed site in a prescribed positional relationship.

The part of the measuring optical system may include a light receiving section for receiving light which is obtained from the prescribed site of the living body, and the light receiving section may be coupled to the measuring optical system securing section at the time of measurement, thereby securing the light receiving section and the prescribed site in a prescribed positional relationship.

The measuring optical system securing section may have an opening, and the prescribed site of the living body may be inserted into the opening.

A measurement condition setting method according to the present invention for setting measurement conditions including a positional relationship between a prescribed site of a living body and a measuring optical system at desirable conditions using a measurement condition setting fixture, in measurement of living body information including irradiating the prescribed site with light from the measuring optical system and obtaining living body information based on the light obtained from the prescribed site; the measurement condition setting fixture including a measurement site securing section attached to the prescribed site, and a measuring optical system securing section, to which a part of the measuring optical system is detachably attachable, for securing the part of the measuring optical system and the prescribed site in a prescribed positional relationship when the part of the measuring optical system is coupled to the measuring optical system securing section, the measurement condition setting method comprising the steps of attaching the part of the measuring optical system to the measuring optical system securing section of the measurement condition setting fixture at the time of measurement, thereby realizing the desirable measurement conditions; and detaching the measuring optical system from the measurement condition setting fixture when no measurement is performed. Thus, the above-described objectives are achieved.

The part of the measuring optical system may include a light irradiation section for irradiating the prescribed site of the living body with light to be directed thereto, and the light irradiation section may be coupled to the measuring optical system securing section at the time of measurement, thereby securing the light irradiation section and the prescribed site in a prescribed positional relationship.

The part of the measuring optical system may include a light receiving section for receiving light which is obtained from the prescribed site of the living body, and the light receiving section may be coupled to the measuring optical system securing section at the time of measurement, thereby securing the light receiving section and the prescribed site in a prescribed positional relationship.

The measuring optical system securing section may have an opening, and the prescribed site of the living body irradiated by the light may be inserted into the opening.

A living body information measuring apparatus according to the present invention for irradiating a prescribed site of a living body with light and obtaining living body information based on the light obtained from the prescribed site, the apparatus comprising a measuring optical system for irradiating the prescribed site with light and receiving the light obtained from the prescribed site; a measurement condition setting fixture having a measurement site securing section attached to the prescribed site, and a measuring optical system securing section, to which a part of the measuring optical system is detachably attachable, for securing the part of the measuring optical system and the prescribed site in a prescribed positional relationship; an arithmetic operation processing section for performing an arithmetic operation on the living body information based on an intensity of the light obtained from the prescribed site and received by the measuring optical system; and an output section for outputting the living body information obtained as a result of the arithmetic operation, wherein the part of the measuring optical system is coupled to the measuring optical system securing section of the measurement condition setting fixture at the time of measurement, thereby setting measurement conditions including a positional relationship between the prescribed site of the living body and the measuring optical system at desirable conditions; and the measuring optical system is detached from the measurement condition setting fixture when no measurement is performed. Thus, the above-described objectives are achieved.

The part of the measuring optical system may include a light irradiation section for irradiating the prescribed site of the living body with light to be directed thereto, and the light irradiation section may be coupled to the measuring optical system securing section at the time of measurement, thereby securing the light irradiation section and the prescribed site in a prescribed positional relationship.

The part of the measuring optical system may include a light receiving section for receiving light which is obtained from the prescribed site of the living body, and the light receiving section may be coupled to the measuring optical system securing section at the time of measurement, thereby securing the light receiving section and the prescribed site in a prescribed positional relationship.

The measuring optical system securing section may have an opening, and the prescribed site of the living body may be inserted into the opening.

The measuring optical system may have an integrating sphere.

The measuring optical system may have an optical fiber.

BRIEF DESCRIPTION OF DRAWINGS

FIGS. 1A and 1B are views schematically illustrating an exemplary structure of a living body information measuring apparatus according to the present invention. FIG. 1A shows the state when no measurement is performed, and FIG. 1B shows the state at the time of measurement.

FIGS. 4A and 4B are views schematically illustrating another exemplary structure of a living body information measuring apparatus according to the present invention.

FIG. 4A shows the state when no measurement is performed, and

FIG. 4B shows the state at the time of measurement.

BEST MODE FOR CARRYING OUT THE INVENTION

Figure 2:
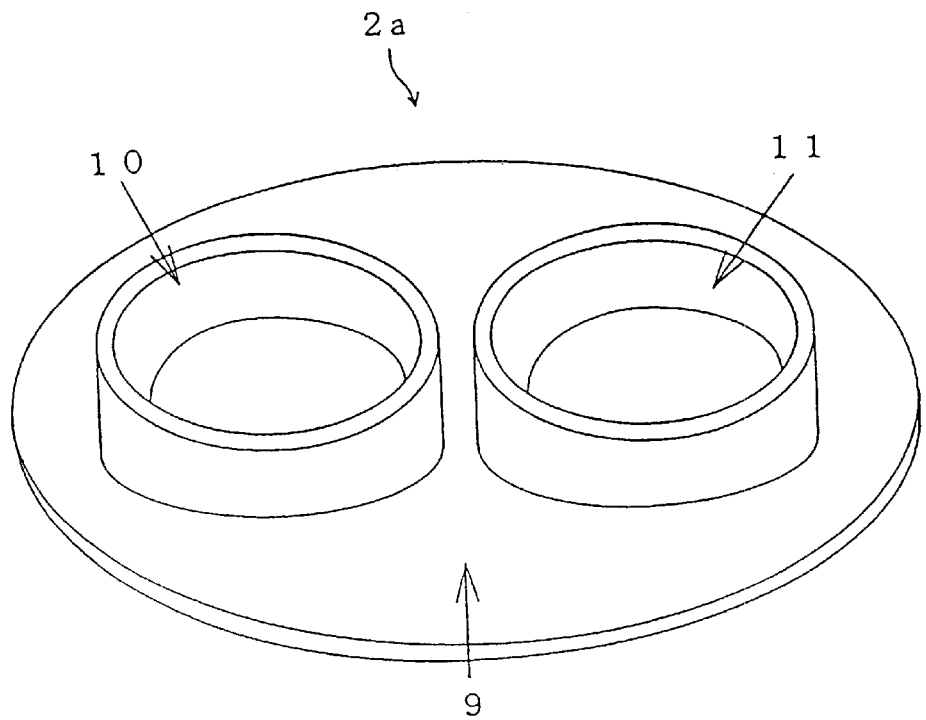
FIG. 2 is a view illustrating an exemplary measurement condition setting fixture according to the present invention.

A measurement condition setting fixture according to the present invention is used for securing together a measuring optical system and a site to be irradiated by light from a living body, when living body information is optically measured. The measurement condition setting fixture includes a measurement site securing section which is secured to the measurement site of the living body for defining a relative position, angle and surface area of the measurement site. Basically, the measurement condition setting fixture is always secured to the measurement site of the living body via, for example, an adhesive tape or a securing band. Alternatively, the measurement site securing section can be an opening. In this case, the measurement condition setting fixture and the measurement site are secured to each other by putting the measurement site in the opening.

The measurement condition setting fixture also includes a securing section for a measuring optical system, the securing section being secured to the measurement site securing section. A part of the measuring optical system is attached to the securing section for the measuring optical system only at the time of measurement. Thus, throughout the measurement, measurement conditions, such as the angle at which the light is incident on the measurement site, the distance between a light irradiation section of the measuring optical system and the measurement site, the distance between the measurement site and a light receiving section for receiving the light from the measurement site, and the positional relationship between the light receiving section and the measurement site can be maintained at desirable conditions; e.g., the measurement conditions which provide a most precise measuring value.

As described above, when the measurement condition setting fixture according to the present invention is used, the positional relationship between the securing section for the measuring optical system and the measurement site securing section secured to the measurement site of the living body does not change. Accordingly, even when the measuring optical system is detached from the measurement condition setting fixture and then reattached, the desirable conditions can be reproduced easily and accurately merely by keeping only the measurement condition setting fixture secured to the measurement site of the living body. Therefore, when the measurement condition setting fixture according to the present invention is used, even in the case where the measurement of the living body information is repeated a plurality of times, the measurement conditions can always be reproduced. Thus, a highly precise measurement value with little deviation among measurements in a series can be obtained.

Provided as the measuring optical system securing section are a securing section for a light irradiation section to which the light irradiation section of the measuring optical system is to be coupled, and a securing section for a light receiving section to which the light receiving section is to be coupled. In the case where a measuring optical system in which the light irradiation section is the same body as the light receiving section, such as a measuring optical system using a random fiber or an integrating sphere, is used, only one securing section is required. The measuring optical system securing section and a part of the measuring optical system are coupled to each other by an insertion system, a threading system or the like. Alternatively, a magnetic force can be used.

A living body information measuring apparatus according to the present invention includes a measuring optical system and the above-described measurement condition setting fixture. First, prior to the measurement, the measurement condition setting fixture is attached to a measurement target, i.e., the site of the living body to be irradiated by light, and a part of the measuring optical system is coupled to the measurement condition setting fixture. In this state, the living body is irradiated by light from the light irradiation section of the measuring optical system, and the resulting transmitted light, reflected light or scattered light is received by the light receiving section of the measuring optical system. By performing an arithmetic operation based on the intensity of the light received by the light receiving section, living body information can be obtained. The obtained living body information is output through an output section.

The living body information measuring apparatus according to the present invention includes the above-described measurement condition setting fixture. Therefore, the measurement conditions can be maintained at the desirable conditions throughout the measurement. Even when substantially the same measurement is repeated a plurality of times, the desirable measurement conditions can be reproduced easily and accurately by repeating the above-described processing while the measurement condition setting fixture is kept secured to the living body. Accordingly, each time a measurement is completed, the measuring optical system can be detached from the measurement condition setting fixture. If necessary, after each measurement is completed, a background measurement is performed in the state where the measuring optical system is detached from the measurement condition setting fixture.

Hereinafter, embodiments of a measurement condition setting fixture and a living body information measuring apparatus according to the present invention will be described with reference to drawings.

EXAMPLE 1

FIGS. 1A and 1B are views schematically illustrating a living body information measuring apparatus in this example. FIG. 1A shows the state when measurement is not performed, and FIG. 1B shows the state at the time of measurement.

A living body information measuring apparatus 100 in this example includes a measurement condition setting fixture 2 attached to a measurement site 1 of a living body, a measuring optical system, an arithmetic operation processing section 7, and an output section 8. The measuring optical system includes a light irradiation section 3 for irradiating the measurement site 1 with light, a projecting optical system 4 for projecting light from a light source (not shown) to the light irradiation section 3, a light receiving section 5 for receiving light reflected by the measurement site 1, and a light receiving optical system 6 for detecting the intensity of the light received by the light receiving section 5. In this example, the light irradiation section 3 and the light receiving section 5 are coupled to the measurement condition setting fixture 2. The arithmetic operation processing section 7 performs an arithmetic operation of the intensity of the reflected light obtained by the light receiving optical system 6 and thus obtains living body information regarding the measurement site 1. The living body information is output via the output section 8.

An example of the measurement condition setting fixture 2 according to the present invention is shown in FIG. 2. A measurement condition setting fixture 2a shown in FIG. 2 can be used as the measurement condition setting fixture 2a of the living body information measuring apparatus 100 shown in FIGS. 1A and 1B. The measurement condition setting fixture 2a includes a measurement site securing section 9 and two securing sections 10 and 11 as measuring optical system securing sections. The measurement condition setting fixture 2a is designed so that relative positions of elements of the measuring optical system with respect to the measurement site 1 be optimal as long as the securing section 9 is attached to the measurement site 1 and the light irradiation section 3 and the light receiving section 5 are respectively coupled to the securing sections 10 and 11. The positional relationship among the three securing sections 9, 10 and 11 does not change. Such a measurement condition setting fixture 2a can be produced by integral processing using, for example, a metal material or a resinous material.

The measurement site securing section 9 is secured to the measurement site 1 by, for example, an adhesive tape or a securing band. Regarding the system for respectively attaching the light irradiation section 3 and the light receiving section 5 of the measuring optical system to the light irradiation section securing section 10 and the light receiving section securing section 11, any system for conducting attachment and detachment in a simple manner can be used. An insertion system, a threading system, a system using a magnet or the like can be used.

The measurement condition setting fixture 2a shown in FIG. 2 is used together with a measuring optical system as shown in FIGS. 1A and 1B which uses the light irradiation section and the light receiving section as two spaced-apart, separate elements. In contrast, in the case where the measuring optical system hag a member acting both as a light irradiation section and a light receiving section, the measurement condition setting fixture can have only one measuring optical system securing section. As an example of such a measurement condition setting fixture, FIG. 3 shows a measurement condition setting fixture 2b having the measurement site securing section 9 and a measuring optical system securing section 10b.

Figure 3:
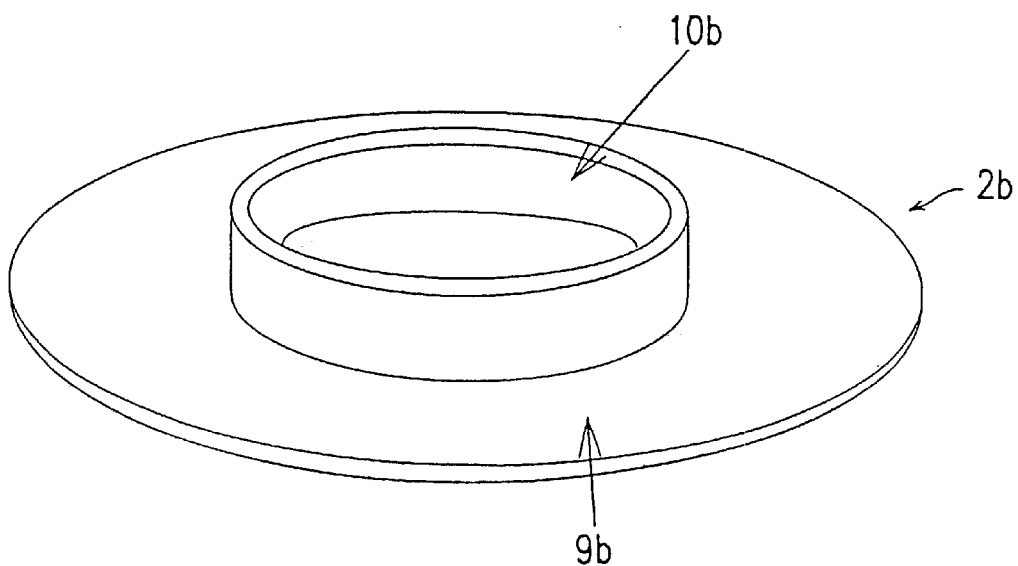
FIG. 3 is a view illustrating another exemplary measurement condition setting fixture according to the present invention.
Figure 8:
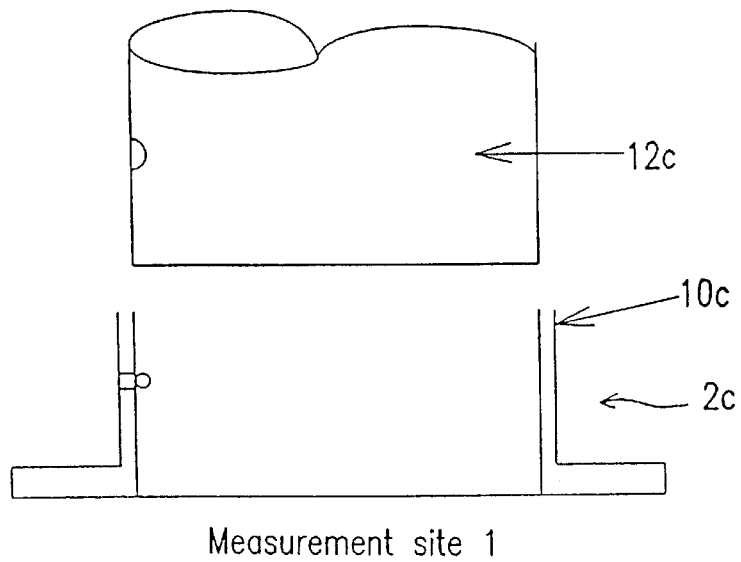
FIG. 8 is a view illustrating still another exemplary measurement condition setting fixture.

In the case where the measuring optical system has a member acting both as a light irradiation section and a light receiving section, measurement condition setting fixtures having structures shown in FIGS. 8 through 12 can be used in lieu of the measurement condition setting fixture 2b shown in FIG. 3. FIG. 8 shows an example in which a recess is formed in a part of an outer wall of a fiber 12c acting both as a light irradiation section and a light receiving section, and a projection is provided on a part of an inner wall of a measuring optical system securing section 10c of a measurement condition setting fixture 2c. The measurement condition setting fixture 2c is secured to the measurement site 1 by an adhesive tape, a securing band or the like as the above-mentioned measurement condition setting fixture 2a. The measurement is performed in the state where the fiber 12c is inserted into the measuring optical system securing section 10c and the recess of the fiber 12c and the projection of the measuring optical system securing section 10c are engaged with each other. Accordingly, throughout the measurement, measurement conditions can be maintained such as the angle at which the light is incident on the measurement site 1, the angle at which the measuring optical system receives the reflected light (diffused light) from the measurement site 1, and the distance from the light source and a light receiving element (neither is shown) in the measuring optical system to the measurement site 1. In the case where the measurement is repeated, the same measurement conditions can be reproduced merely by putting the recess of the fiber 12c into engagement with the projection of the measuring optical system securing section 10c.

Figure 9:
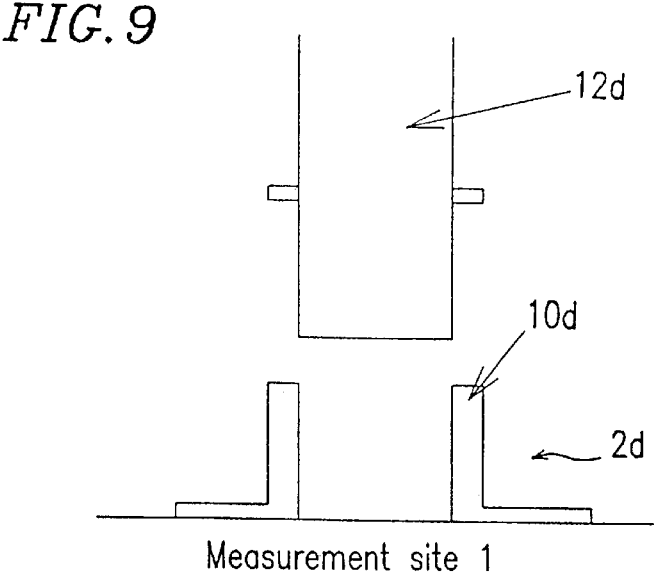
FIG. 9 is a view illustrating still another exemplary measurement condition setting fixture.

In the example shown in FIG. 9, a projection is provided on an outer wall of a fiber 12d acting both as a light irradiation section and a light receiving section. The projection is provided so that the distance from a tip of the fiber 12d to the projection is substantially equal to the depth of a measuring optical system securing section 10d of a measurement condition setting fixture 2d. Accordingly, when the fiber 12d is inserted into the measuring optical system securing section 10d for performing measurement, the projection of the fiber 12d is located on a top edge of the securing section 10d. The fiber 12d can have one projection on the outer wall of the fiber 12d or a plurality of projections on both sides. Alternatively, the fiber 12d can have a circular projection surrounding the outer wall. In any case, the fiber 12d is positioned merely by inserting the fiber 12d into the measuring optical system securing section 10d.

In this manner, the same measurement conditions can be reproduced repeatedly.

Figure 10:
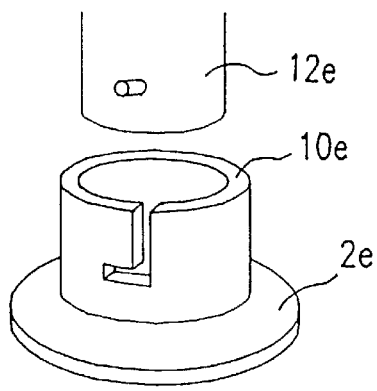
FIG. 10 is a view illustrating still another exemplary measurement condition setting fixture.

In the example shown in FIG. 10, a fiber 12e having a projection on an outer wall thereof is used. This example is different from the example shown in FIG. 9 in that the fiber 12e and a measurement condition setting fixture 2e are secured with respect to each other by forming an L-shaped cutout in the measuring optical system securing section 10e of the measurement condition setting fixture 2e and fitting the projection of the fiber 12e into the L-shaped output. By using the fiber 12e and the measurement condition setting fixture 2e having such a structure, the fiber 12e can be easily and accurately positioned and secured. The same measurement conditions can be reproduced repeatedly.

Figure 11:
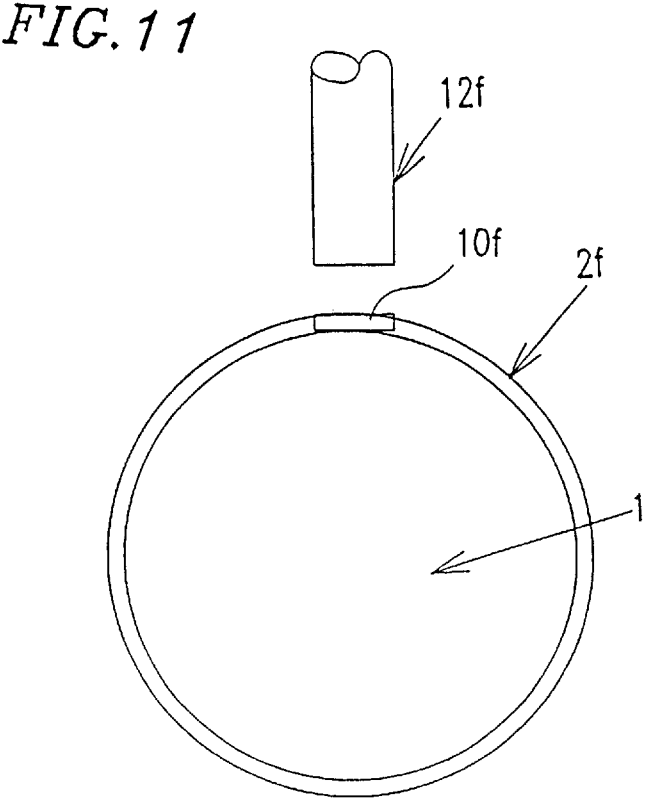
FIG. 11 is a view illustrating still another exemplary measurement condition setting fixture.

In the above-described examples, the measurement condition setting fixtures 2a, 2b, 2e, 2d and 2e are secured to the measurement site 1 by an adhesive tape, a securing band or the like. The manner of securing is not limited to these. For example, the measurement condition setting fixture itself can have a capability to be secured to the measurement site. FIG. 11 shows a circular measurement condition setting fixture 2f. The setting fixture 2f is used when, for example, the measurement site 1 is a part of an arm. The arm is inserted into the setting fixture 2f. A measuring optical system securing section 10f is provided on a part of a circumferential surface of the measurement condition setting fixture 2f formed of rubber. When a fiber 12f is inserted into the measuring optical system securing section 10f, the fiber 12f is secured with respect to the measurement site 1. In this example, the setting condition setting fixture 2f is secured to the measurement site 1 by the contraction of the rubber, and the fiber 12f as a part of the measuring optical system is also secured to the measurement condition setting fixture 2f by the contraction of the rubber. Accordingly, the measurement conditions do not change during the measurement. In the case where the measurement is repeated, the same measurement conditions can be repeatedly reproduce easily and accurately. The measurement condition setting fixture 2f formed of rubber can be circular or cylindrical.

Figure 12:
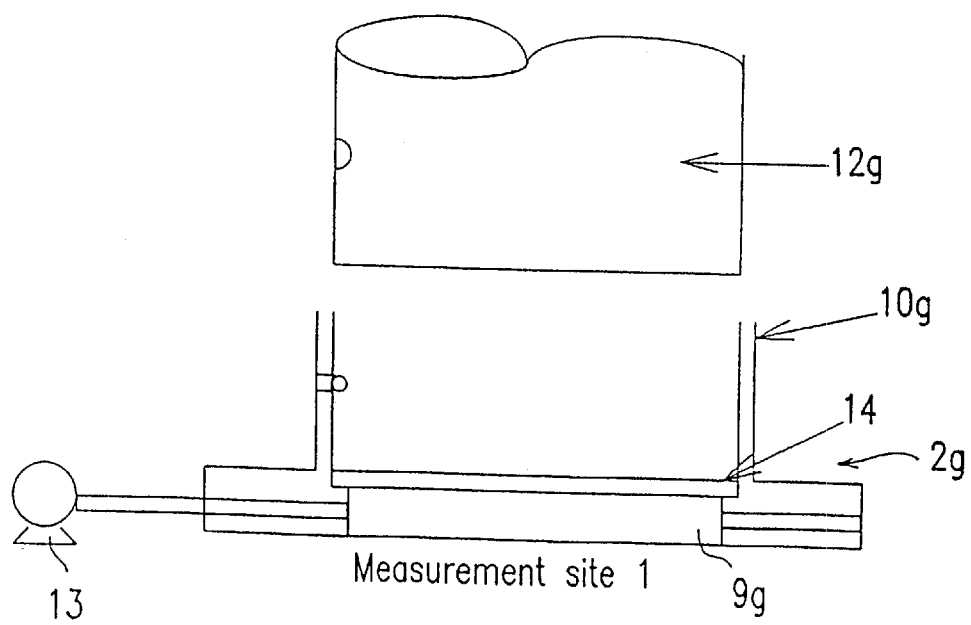
FIG. 12 is a view illustrating still another exemplary measurement condition setting fixture.

Another example of a measurement condition setting fixture having a capability to be secured will be described. FIG. 12 shows a measurement condition setting fixture 2g having a measurement site securing section 9g and a measuring optical system securing section 10g. The securing section 9g and the securing section 10g are separated from each other by a transparent plate 14 formed of glass or the like. The measurement site 1 is irradiated by light from the fiber 12g attached to the securing section 10g via the transparent plate 14. The setting fixture 2g further has a pump 13 which is connected to the measurement site securing section 9g. When the measurement site securing section 9g is placed on the measurement site 1, the pump 13 decreases the pressure in the space surrounded by an inner wall of the measurement site securing section 9g, the transparent plate 14, and the measurement site 1, and thus secures the setting fixture 2g and the measurement site 1 to each other. The measuring optical system securing section 10g and the fiber 12g as a part of the measuring optical system are secured to each other in the same manner as in the example shown in FIG. 8. In this manner, the measuring optical system is secured to the measurement site 1. Accordingly, the measurement conditions do not change during the measurement. Even when the measuring optical system is detached from the measurement condition setting fixture 2g each time a measurement is completed while the measurement is repeated a plurality of times, the same measurement conditions can be reproduced.

With reference to FIGS. 1A and 1B, a living body information measuring apparatus in this example will be described.

As described above, the measuring optical system includes the projecting optical system 4 having the light irradiation section 3 for irradiating the measurement site 1 of a living body with light and a light source (not shown) so as to guide the light from the light source to the light irradiation section 3; and the light receiving optical system 6 having the light receiving section 5 for receiving the light reflected (scattered) by the measurement site 1 and a photodetector (not shown) so as to guide the light received by the light receiving section 5 to the photodetector. In addition to the light source, the projecting optical system 4 has a light splitting device for splitting the light emitted by the light source into a spectrum, and an optical fiber. The split light propagating through the optical fiber is guided to the light irradiation section 3.

The light receiving optical system 6 also has a light splitting device for splitting the light received by the light receiving section 5, and an optical fiber for guiding the light to the photodetector, in addition to the photodetector for detecting the intensity of the received light. The light receiving optical system 6 further includes an interface circuit for amplifying the output from the photodetector and converting the output into a digital signal. The intensity of the output from the interface circuit is in correspondence with the intensity of the light absorbed in accordance with the living body information with respect to the measurement site 1. The intensity of the output from the interface circuit is sent to the arithmetic operation controlling section 7.

In this example, the light irradiation section 2 and the light receiving section 5 in the measuring optical system are attached to the measurement condition setting fixture 2 and thus secured to the measurement site 1. The shape of a part of the measuring optical system which is attached to the measurement condition setting fixture 2 is designed in accordance with the shape of the measurement condition setting fixture 2 as described with reference to FIGS. 2, 3 and 8 through 12. In other words, the light irradiation section 3 and the light receiving section 5 can be provided to be adjacent to each other and attached to a single measuring optical system securing section of the measurement condition setting fixture 2. Alternatively, the light irradiation section 3 and the light receiving section 5 can be provided to be spaced apart from each other and respectively attached to different measuring optical system securing sections (light irradiation section securing section and the light receiving section securing section).

As described above, the light irradiation section 3 and the light receiving section 5 can be formed of a single member using an integrating sphere or an optical fiber. In such a case, the measurement condition setting fixture 2 requires only one measuring optical system securing section, needless to say.

The arithmetic operation controlling section 7 has a microcomputer and performs an arithmetic operation on a digital signal which is input from the interface circuit of the measuring optical system. Thus, the living information in a target living body is calculated. The calculated living body information is output to the output section 8 including, for example, a CRT display and a printer.

The arithmetic operation controlling section 7 generates a control signal and supplies the control signal to the measuring optical system and the output section 8. The control signal controls the operations of the light source, the light splitting device, and the interface circuit in the measuring optical system, and the output section 8.

The measurement of the living body information using the living body information measuring apparatus shown in FIGS. 1A and 1B is performed in the following manner.

First, the measurement site securing section 9 of the measurement condition setting fixture 2 is secured to an arbitrary measurement site 1 of the living body. Next, prior to the start of the measurement, a part of the measuring optical system is attached to the measuring optical system securing section of the measurement condition setting fixture 2. In the case where the measurement condition setting fixture 2 shown in FIG. 2 is used, the light irradiation section 3 and the light receiving section 5 are respectively attached to the light irradiation section securing section 10 and the light receiving section securing section 11. Thus, both the projecting optical system 4 and the receiving optical system 6 are secured to the measurement site 1. The measurement site 1, the projecting optical system 4 and the receiving optical system 6 are located at preferable relative positions. Such relative positions are set at positions where a most sensitive and precise measurement is performed.

The measurement site 1 is irradiated with the light from the light source of the projecting optical system 4 through the light irradiation section 3 in such a state. The light reflected (scattered) by the measurement site 1 is incident on the light receiving section 5 and reaches the photodetector of the light receiving optical system 6. The photodetector converts the received light into an electric signal corresponding to the intensity of the light. The electric signal is converted into a digital signal by the interface circuit and then sent to the arithmetic operation controlling section 7. The arithmetic operation controlling section 7 detects the living body information with respect to the living body, for example, the concentration of the target component in the living body based on the digital signal, and displays the information on a display in the output section 8 or prints out the information by means of a printer.

After the completion of the measurement, the light irradiation section 3 and the light receiving section 5 are detached from the measuring optical system securing section of the measurement condition setting fixture 2. Thus, the measuring optical system is detached from the measurement site 1 of the living body.

If necessary, the background measurement is performed thereafter. By repeating such an operation, preferable measurement conditions can be reproduced with satisfactory reproducibility, and measurement results with good reproducibility can be obtained.

By using the measurement condition setting fixture 2 according to the present invention, the measurement site 1 can be reproduced accurately. Accordingly, conditions such as, for example, the surface area of the measurement site, the surface information, and living body information on the internal tissues can be maintained. The relative position of the measuring optical system with respect to the measurement site 1 is constantly set at a preferable relative position accurately. Accordingly, conditions such as, for example, the reflectance, the transmittance, the optical path length, and pressure applied on the measurement site in the case of stray light can be maintained.

Figure 6:
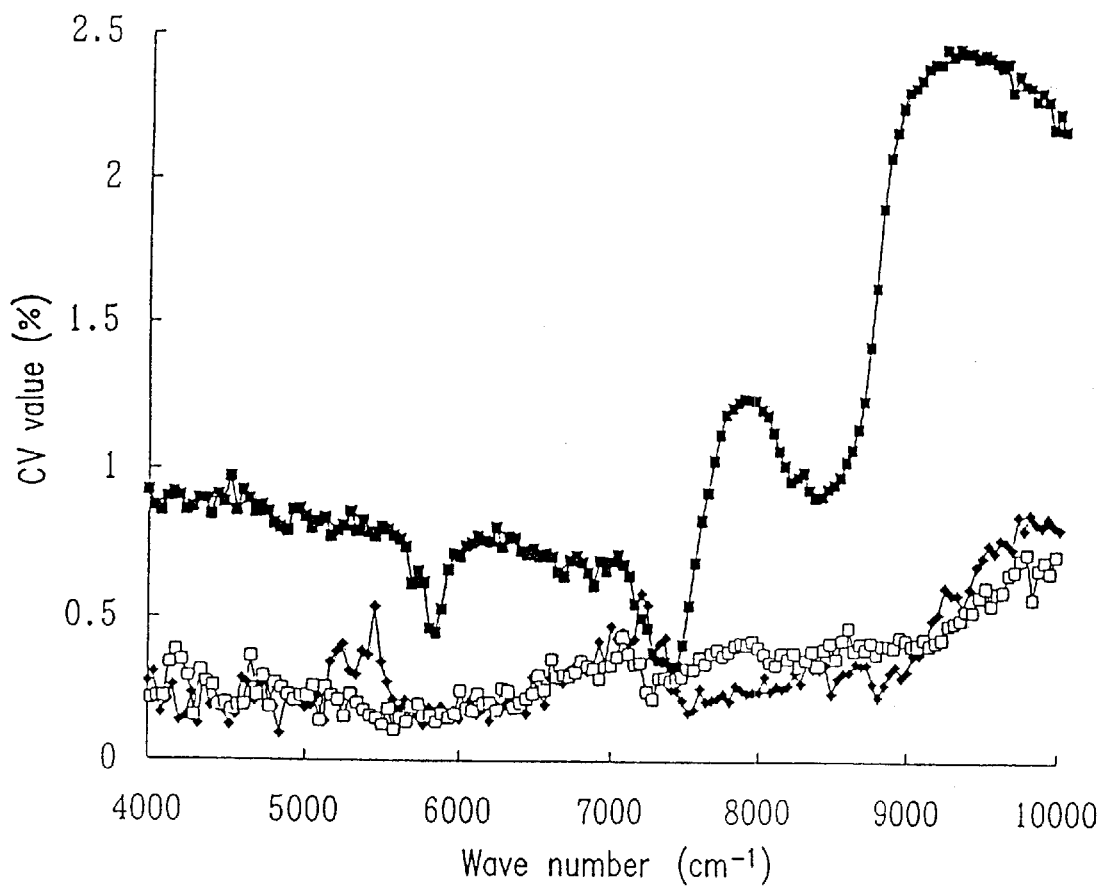
FIG. 6 is a view illustrating deviation of diffuse reflection on a surface of a human hand measured by a living body information measuring apparatus using an integrating sphere as CV value spectra.

FIG. 6 is a graph illustrating the reproducibility obtained when the light diffuse-reflected by the surface of a human hand was measured by the living body information measuring apparatus in which the light irradiation section 3 and the light receiving section 5 are formed of a single integrating sphere. An energy spectrum was measured ten times for each of the cases where neither the measurement site nor the measuring optical system was secured and both were re-located for each measurement, where the measurement site was kept secured to the measuring optical system, and where the measurement site was re-secured for each measurement using the measurement condition setting fixture according to the present invention. In FIG. 6, the obtained energy spectra are represented by curves 301, 302 and 303 as CV value spectra in accordance with wavelength. As can be appreciated from FIG. 6, in the case where the measurement site and the measuring optical system was secured to the measuring optical system using the measurement condition setting fixture according to the present invention (curve 303), the spectrum showed reproducibility which was significantly better than the reproducibility obtained in the case where the measurement site was not secured to the measuring optical system (curve 301) and was about equal to the reproducibility obtained in the case where the living body is secured to the measuring optical system (curve 302).

Figure 7:
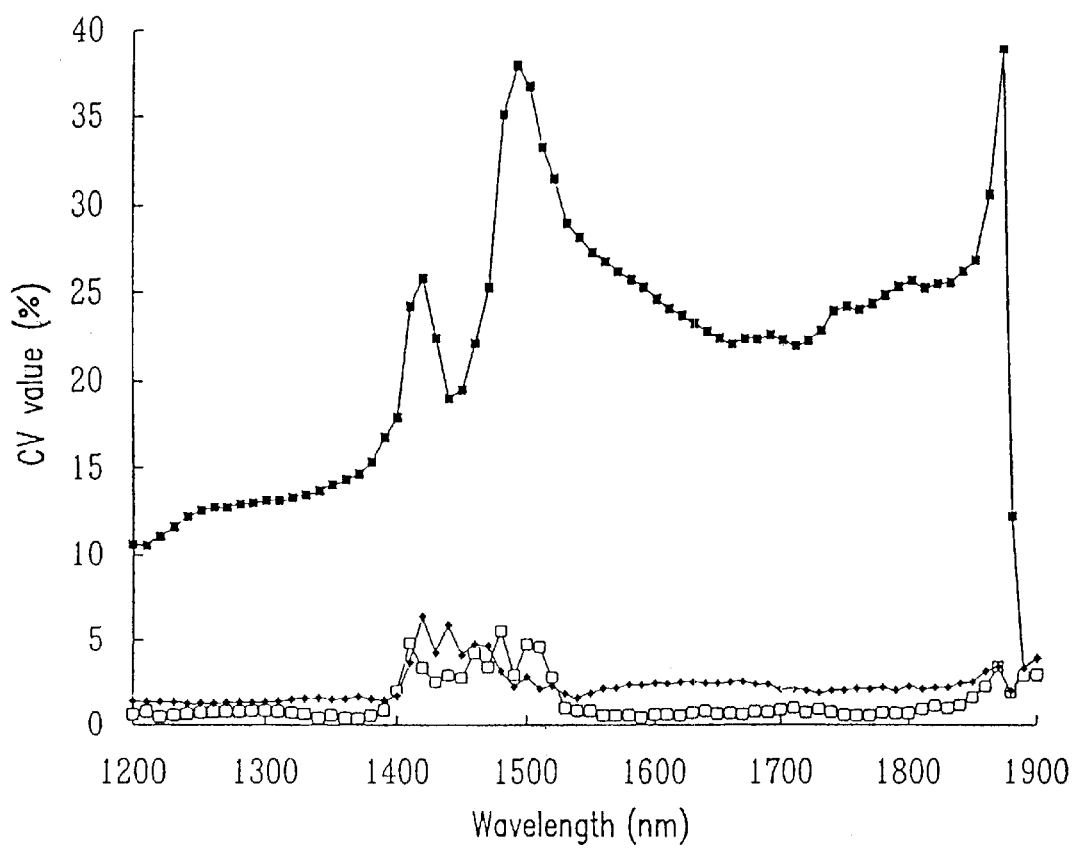
FIG. 7 is a view illustrating deviation of diffuse reflection on a surface of a human hand measured by a living body information measuring apparatus using an optical fiber as CV value spectra.

FIG. 7 shows the CV value spectra obtained when the light diffuse-reflected by the surface of a human hand was measured by the living body information measuring apparatus in which the light irradiation section 3 and the light receiving section 5 were formed of an optical fiber in lieu of the integrating sphere. In this case also, an energy spectrum was measured ten times for each of the cases where neither the measurement site nor the measuring optical system was secured and both were re-located for each measurement, where the measurement site was secured to the measuring optical system in the conventional manner (i.e., without using the measurement condition setting fixture according to the present invention), and where the measurement site and the measuring optical system were secured to each other using the measurement condition setting fixture according to the present invention. As can be appreciated from FIG. 7, when the optical fiber was used also, in the case where the measurement site and the measuring optical system were secured to each other using the measurement condition setting fixture according to the present invention (curve 403), the spectrum showed reproducibility which was significantly better than the reproducibility obtained in the case where the measurement site was not secured to the measuring optical system (curve 401) and was about equal to the reproducibility obtained in the case where the living body was secured to the measuring optical system (curve 402).

EXAMPLE 2

Next, with reference to FIGS. 4A and 4B, a living body information measuring apparatus in a second example will be described. In FIGS. 4A and 4B, identical elements previously discussed with respect to FIG. 1A and 1B bear identical reference numerals and the detailed descriptions thereof will be omitted.

In this example, the measurement condition setting fixture 2 is a ring-shaped or bracelet-shaped. The measurement site 1 and the measurement condition setting fixture 2 are secured to each other by inserting a part of the living body including the measurement site 1 into the setting fixture 2. In this example, the light used for measuring the living body information has been transmitted through the body at the measurement site. Therefore, the light irradiation section 3 and the light receiving section 5 of the measuring optical system are located so as to have the living body therebetween. FIGS. 4A and 4B show respective cross-sections in the state where the measurement condition setting fixture 2 is attached to the living body when measurement is not performed and when measurement is performed.

Figure 5:
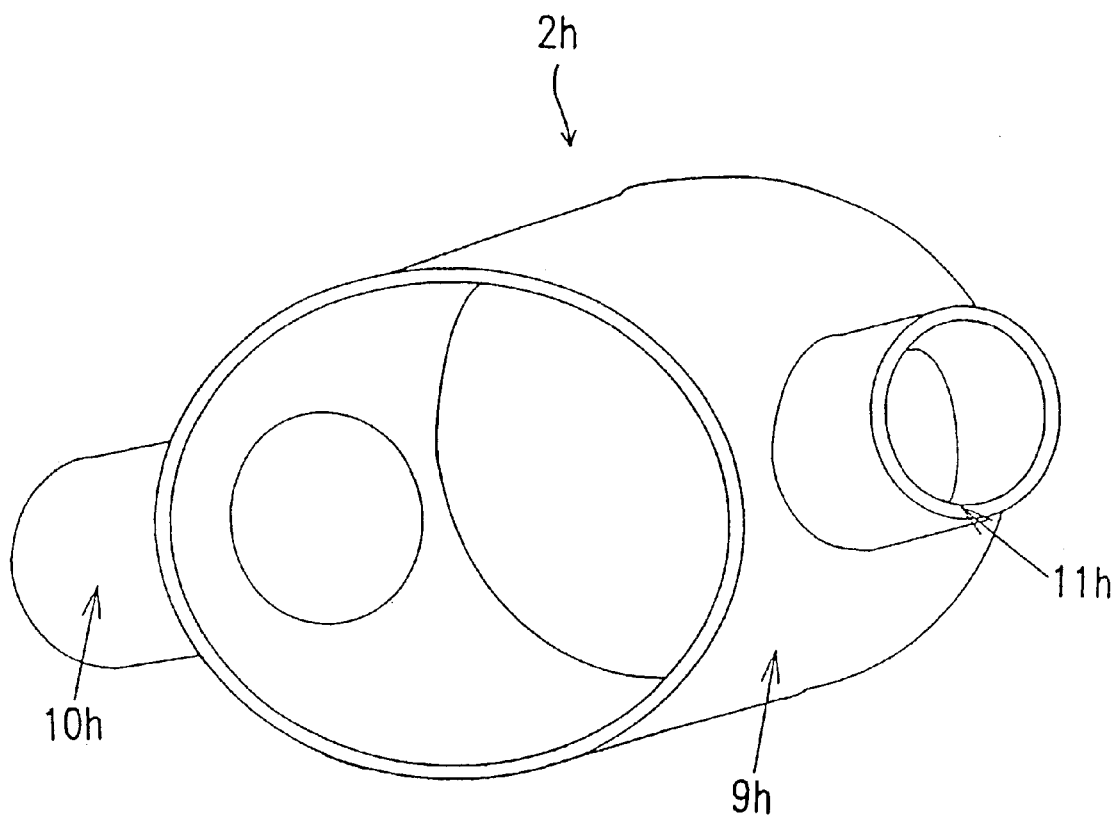
FIG. 5 is a view illustrating still another exemplary measurement condition setting fixture according to the present invention.

As shown in FIG. 4A, prior to the measurement, a part of the living body including a measurement site is first inserted into the measurement condition setting fixture 2 and thus secured. The site is secured using, for example, an adhesive tape, a securing band or the like. FIG. 5 shows an example of a measurement condition setting fixture $2h$ usable in a living body information measuring apparatus for detecting living body information using the transmitted light, as shown in FIG. 4A. A light irradiation section securing section $10h$ and a light receiving section securing section $11h$ which are measuring optical system securing sections are formed on a wall of a cylindrical measurement site securing section $9h$. The securing sections $9h$, $10h$ and $11h$ are secured with respect to one another, and the relative positions thereof do not change. As shown in FIGS. 11 and 12, a measurement condition setting fixture 2 having a capability of being secured itself can be used. Next, as shown in FIG. 4B, the light irradiation section 3 and the light receiving section 5 are respectively attached to the light irradiation section securing section 10 and the light receiving section securing section 11 which are measuring light optical securing sections and then secured. The attachment and securing can be performed by any simple system, for example, a threading system, an insertion system or a system using a magnet.

The light emitted by a light source (not shown) of the projecting optical system 4 is projected to the measurement site 1 of the living body via the light irradiation section 3 in this state, and the light transmitted through the body at the measurement site 1 reaches the light receiving section 5. The light which has reached the light receiving section 5 is converted into an electric signal having an amplitude corresponding to the intensity of the light by a photodetector (not shown) of the light receiving optical system 6, and converted into a digital signal by an interface circuit (not shown) of the light receiving optical system 6. Then, the digital signal is output to the arithmetic operation control section 7. The arithmetic operation control section 7 detects the living body information with respect to the living body, for example, the concentration of a target component, and outputs the result to the output section 8.

Thus, in this example also, the relative positions of the measurement site 1 and the measuring optical system can be maintained throughout the measurement. Accordingly, highly precise measurement results can be obtained with little deviation. In the case where the measurement condition setting fixture $2h$ is kept attached to the part of the living body including the measurement site, even when the measuring optical system is detached from the measurement site 1 after each measurement while the measurement is repeated a plurality of times, desirable measurement conditions can be reproduced easily and accurately. Accordingly, measurement results with satisfactory reproducibility can be obtained.

INDUSTRIAL APPLICABILITY

According to the present invention, a measurement condition setting fixture is secured to the measurement site. At the time of measurement, a measuring optical system is secured to the setting fixture; and when no measurement is performed, the measuring optical system is detached. Thus, the measurement site can be repetitively returned to easily and accurately, and the relative position of the measuring optical system with respect to the measurement site can be repetitively reproduced easily and accurately. Since the living body is soft and highly flexible, attachment and detachment of the measuring optical system with respect to the living body tended to result in failure to return to a correct measurement site. However, according to the present invention, a measurement condition setting fixture is used, and the measurement condition setting fixture and the measuring optical system are attached to each other or detached from each other mechanically. Thus, more accurate reproduction of the measurement site can be performed.

According to the present invention, the light irradiation section securing section of the measurement condition setting fixture secured in advance to the measurement site of the living body and the light irradiation section of the measuring optical system are secured to each other at the time of measurement and detached from each other when no measurement is performed. Thus, the measurement site, and the relative position of the light irradiation section with respect to the measurement site, can be repetitively reproduced easily and accurately.

Moreover, according to the present invention, the light receiving section securing section of the measurement condition setting fixture secured in advance to the measurement site of the living body and the light receiving section of the measuring optical system are secured to each other at the time of measurement and detached from each other when no measurement is performed. Thus, the measurement site, and the relative position of the light receiving section of the measuring optical system with respect to the measurement site, can be repetitively reproduced easily and accurately.

Moreover, according to the present invention, the light irradiation section and the light receiving section of the measuring optical system are respectively secured to the light irradiation section securing section and the light receiving section securing section of the measurement condition setting fixture secured in advance to the measurement site of the living body, and are detached therefrom when no measurement is performed. Thus, the measurement site, and the relative position of the measuring optical system with respect to the measurement site, can be repetitively reproduced easily and accurately.

Moreover, according to the present invention, the measurement site is accurately reproduced by the measurement condition setting fixture. Thus, measurement conditions such as the surface area of the measurement site, surface information, and living body information about internal tissues can be maintained.

Moreover, according to the present invention, the relative positions of the measuring optical system with respect to the measurement site is accurately reproduced by the measurement condition setting fixture. Therefore, measurement conditions such as reflectance and transmittance at the measurement site, length of the optical path, and pressure applied to the measurement site in the case of stray light can be maintained.

Moreover, according to the present invention, the above-described measurement conditions are accurately reproduced by the measurement condition setting fixture. Accordingly, transmitted light, reflected light or scattered light with a small cause of error can be obtained from the living body. By obtaining the living body information with respect to the living body based on the intensity of such light with a small cause of error through arithmetic operation processing, the living body information with respect to the living body can be measured with high reproducibility.

Moreover, according to the present invention, a simple-structured measurement condition setting fixture which is commonly usable for any measurement target can be provided.

What is claimed is:

1. A measurement condition setting fixture for setting measurement conditions, including a positional relationship between a prescribed site of a living body and a measuring optical system at desirable conditions in measurement of living body information, including irradiating the prescribed site with light from the measuring optical system and obtaining living body information based on the light obtained from the prescribed site, the measurement condition setting fixture comprising:
    a measurement site securing section that can be attached to the prescribed site; and
    at least one measuring optical system securing section, which is adapted for having selectively coupled thereto a part of the measuring optical system, for securing the part of the measuring optical system and the prescribed site in a prescribed positional relationship when the part of the measuring optical system is coupled to the measuring optical system securing section,
        wherein the part of the measuring optical system is coupled to the at least one measuring optical system securing section at the time of measurement thereby realizing the desirable measurement conditions, and the part of the measuring optical system is detached from the measuring optical system securing section when no measurement is performed, and
        wherein the positional relationship between the prescribed site of the living body and the measuring optical system does not change when the part of the measuring optical system is attached, detached and then reattached to the at least one measuring optical system securing section.

2. A measurement condition setting fixture according to claim 1, wherein the at least one measuring optical system securing section includes an opening that can be positioned to allow the measurement of living body information at the prescribed site of the living body.

3. A measurement condition setting fixture according to claim 1, where in the at least one measuring optical system securing section comprises two measuring optical system securing sections that are arranged relative to the measurement site securing section to allow the measurements of living body information at the prescribed site of the living body.

4. A measurement condition setting fixture according to claim 1, wherein the at least one measuring optical system securing section comprises two measuring optical system securing sections that are arranged next to one another relative to the measurement site securing section to allow the measurements of living body information based on light reflected within the living body.

5. A measurement condition setting fixture according to claim 1, wherein the at least one measuring optical system securing section comprises two measuring optical system securing sections that are arranged opposite to one another relative to the measurement site securing section to allow the measurements of living body information based on light transmitted through the living body.

6. A measurement condition setting fixture according to claim 1, wherein the at least one measuring optical system securing section consists of one measuring optical system securing section that is arranged relative to the measurement site securing section to allow the measurements of living body information at the prescribed site of the living body.

7. A measurement condition setting fixture according to claim 1, wherein the measurement site securing section has a planar or approximately planar shape.

8. A measurement condition setting fixture according to claim 1, wherein the measurement site securing section has a cylindrical or approximately cylindrical shape.

9. A measurement condition setting fixture according to claim 1, wherein the measurement site securing section has a circular or approximately circular shape.

10. A measurement condition setting fixture according to claim 1, wherein each measuring optical system securing section further includes a projection that can be removably attached to a respective recess in the part of the measuring optical system.

11. A measurement condition setting fixture according to claim 1, wherein each measuring optical system securing section comprises a cylinder having a top edge that can be removably attached to a respective projection in the part of the measuring optical system.

12. A measurement condition setting fixture according to claim 1, wherein each measuring optical system securing section further includes a cut-out section that can be removably attached to a respective projection in the part of the measuring optical system.

13. A measurement condition setting fixture according to claim 1, wherein the measurement site securing section has a circumferential surface.

14. A measurement condition setting fixture according to claim 13, wherein each measuring optical system securing section further includes a section made of rubber that can be removably attached to the part of the measuring optical system.

15. A measurement condition setting fixture according to claim 1, further comprising a transparent plate positioned between a respective measuring optical system securing section and the measurement site securing section such that a gap can be created between the transparent plate and the prescribed site on the living body at the time of measurement; whereby, pressure in the gap can be decreased to secure the measurement condition setting fixture relative to the prescribed site at the time of measurement.

16. A measurement condition setting fixture according to claim 1, wherein the measurement site securing section and the at least one measuring optical system securing section comprise an integral unit.

17. A living body information measuring apparatus for irradiating a prescribed site of a living body with light and obtaining living body information based on the light obtained from the prescribed site, the apparatus comprising:
  a measuring optical system for irradiating the prescribed site with light and receiving the light obtained from the prescribed site;
  a measurement condition setting fixture having a measurement site securing section that can be attached to the prescribed site, and a measuring optical system securing section, which is adapted for having selectively coupled thereto a part of the measuring optical system, for securing the part of the measuring optical system and the prescribed site in a prescribed positional relationship;
  an arithmetic operation processing section for performing an arithmetic operation on the living body information based on an intensity of the light emitted from the prescribed site and received by the measuring optical system; and
  an output section for outputting the living body information obtained as a result of the arithmetic operation,
    wherein the part of the measuring optical system is coupled to the measuring optical system securing section of the measurement condition setting fixture at the time of measurement, thereby setting measurement conditions including a positional relationship between the prescribed site of the living body and the measuring optical system at the desirable conditions; and the measuring optical system is detached from the measurement condition setting fixture when no measurement is performed, and
    wherein the positional relationship between the prescribed site of the living body and the measuring optical system does not change when the part of the measuring optical system is attached, detached and then reattached to the measuring optical system securing section.

18. A living body information measuring apparatus according to claim 17, wherein the measuring optical system securing section has an opening, and the prescribed site of the living body can be inserted into the opening.

19. A living body information measuring apparatus according to claim 17, wherein the measuring optical system has an integrating sphere.

20. A living body information measuring apparatus according to claim 17, wherein the measuring optical system has an optical fiber.

21. A living body information measuring apparatus according to claim 20, wherein the optical fiber includes a recess or projection that is removably attachable to the measuring optical system securing section.

22. A living body information measuring apparatus according to claim 17, wherein the measurement site securing section and the measuring optical system securing section each comprise respective means for removably coupling the measurement site securing section and the measuring optical system securing section together at the time of measurement.

23. A measurement condition setting fixture according to claim 1, further comprising the part of the measuring optical system; wherein the part of the measuring optical system includes a light irradiation section for irradiating the prescribed site of the living body with light, and the light irradiation section is coupled to the measuring optical system securing section at the time of measurement, thereby securing the light irradiation section and the prescribed site in a prescribed positional relationship.

24. A measurement condition setting fixture according to claim 1, further comprising the part of the measuring optical system; wherein the part of the measuring optical system includes a light receiving section for receiving light which is obtained from the prescribed site of the living body, and the light receiving section is coupled to the measuring optical system securing section at the time of measurement, thereby securing the light receiving section and the prescribed site in a prescribed positional relationship.

25. A living body information measuring apparatus according to claim 17, wherein the part of the measuring optical system includes a light irradiation section for irradiating the prescribed site of the living body with light, and the light irradiation section is coupled to the measuring optical system securing section at the time of measurement, thereby securing the light irradiation section and the prescribed site in a prescribed positional relationship.

26. A living body information measuring apparatus according to claim 17, wherein the part of the measuring optical system includes a light receiving section for receiving light which is obtained from the prescribed site of the living body, and the light receiving section is coupled to the measuring optical system securing section at the time of measurement, thereby securing the light receiving section and the prescribed site in a prescribed positional relationship.

27. A measurement condition setting fixture for setting measurement conditions, including a positional relationship between prescribed site of a living body and a measuring optical system, at desirable conditions, in measurement with respect to the prescribed site of the living body using a measuring optical system which includes a light irradiation section for irradiating the prescribed site of the living body with light and a light receiving section for receiving light, the measurement condition setting fixture comprising:

a first securing section adapted to be attached to the living body;

a second securing section, which is adapted for having selectively coupled thereto the light irradiation section, for securing the light irradiation section and the prescribed site of the living body in a prescribed positional relationship when the light irradiation section is coupled to the second securing section;

a third securing section adapted to be attached to the living body so that a part of the living body is held between the first securing section and the third securing section; and a fourth securing section, which is adapted for having selectively coupled thereto the light receiving section, for securing the light receiving section and the prescribed section of the living body in a prescribed positional relationship when the light receiving section is coupled to the fourth securing section, wherein the first through fourth securing sections are secured at the time of measurement so that the light irradiation section irradiates the prescribed site of the living body with light and the light receiving section receives light transmitted through the proscribed site of the living body, and wherein the positional relationship between the prescribed site of the living body and the measuring optical system does not change when the light irradiation section and light receiving section are attached, detached and then reattached to, respectively, the second securing section and the fourth securing section.

28. A living body information measuring apparatus for measuring information with respect to a prescribed site of a living body, the apparatus comprising:

a measurement optical system including a light irradiation section for irradiating the prescribed site of the living body with light and a light receiving section for receiving light;

a measurement condition setting fixture for setting measurement conditions, including a positional relationship between the prescribed site of the living body and the measurement optical system, at desirable conditions;

an arithmetic operation processing section for performing an arithmetic operation on information with respect to the prescribed site of the living body based on an intensity of the light received by the light receiving section; and an output section for outputting the information obtained as a result of the arithmetic operation, wherein the measurement condition setting fixture includes:

a first securing section adapted to be attached to the living body;

a second securing section, which is adapted for having selectively coupled thereto the light irradiation section, for securing the light irradiation section and the prescribed site of the living body in a prescribed positional relationship when the light irradiation section is coupled to the second securing section;

a third securing section adapted to be attached to the living body so that a part of the living body is held between the first securing section and the third securing section; and a fourth securing section, which is adapted for having selectively coupled thereto the light receiving section, for securing the light receiving section and the prescribed section of the living body in a prescribed positional relationship when the light receiving section is coupled to the fourth securing section, wherein the first through fourth securing sections are secured at the time of measurement so that the light irradiation section irradiates the prescribed site of the living body with light and the light receiving section receives light transmitted through the prescribed site of the living body, and wherein the positional relationship between the prescribed site of the living body and the measuring optical system does not change when the light irradiation section and light receiving section are attached, detached and then reattached to, respectively, the second securing section and the fourth securing section.

29. A measurement condition setting method for setting measurement conditions including a positional relationship between a prescribed site of a living body and a measuring optical system at desirable conditions using a measurement condition setting fixture, in measurement of living body information including irradiating the prescribed site with light from the measuring optical system and obtaining living body information based on the light obtained from the prescribed site; the measurement condition setting fixture including a measurement site securing section adapted to be attached to the prescribed site, and a measuring optical system securing section, which is adapted for having selectively coupled thereto a part of the measuring optical system, for securing the part of the measuring optical system and the prescribed site in a prescribed positional relationship when the part of the measuring optical system is coupled to the measuring optical system securing section, wherein the positional relationship between the prescribed site of the living body and the measuring optical system does not change when the part of the measuring optical system is attached, detached and then reattached to the measuring optical system securing section, the measurement condition setting method comprising the steps of:

attaching the part of the measuring optical system to the measuring optical system securing section of the measurement condition setting fixture at the time of measurement, thereby realizing the desirable measurement conditions; and detaching the measuring optical system from the measurement condition setting fixture when no measurement is performed.

30. A measurement condition setting method according to claim 29, wherein the part of the measuring optical system includes a light irradiation section for irradiating the prescribed site of the living body with light to be directed thereto, and wherein said attaching step comprises coupling the light irradiation section to the measuring optical system securing section at the time of measurement, thereby securing the light irradiation section and the prescribed site in a prescribed positional relationship.

31. A measurement condition setting method according to claim 29, wherein the part of the measuring optical system includes a light receiving section for receiving light which is obtained from the prescribed site of the living body, and wherein said attaching step comprises coupling the light receiving section to the measuring optical system securing section at the time of measurement, thereby securing the light receiving section and the prescribed site in a prescribed positional relationship.

32. A measurement condition setting method according to claim 29, wherein the measuring optical system securing section has an opening, and further comprising the step of inserting the prescribed site of the living body irradiated by the light into the opening.

* * * * *